(12) United States Patent
Lee et al.

(10) Patent No.: US 9,046,460 B2
(45) Date of Patent: Jun. 2, 2015

(54) PARTICLE MEASURING APPARATUS AND MEASURING METHOD USING THE SAME

(75) Inventors: Yong Koo Lee, Yongin-Si (KR); In Duk Hwang, Inchun (KR); Tae Soo Kim, Yongin-si (KR); Jong Gun Lee, Suwon-si (KR); Seock Woo Jang, Suwon-si (KR); Chul Ho Yun, Suwon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 635 days.

(21) Appl. No.: 13/337,369

(22) Filed: Dec. 27, 2011

(65) Prior Publication Data
US 2012/0185211 A1      Jul. 19, 2012

(30) Foreign Application Priority Data
Jan. 17, 2011     (KR) .......................... 10-2011-0004545

(51) Int. Cl.
*G06F 19/00*     (2011.01)
*G01N 15/02*     (2006.01)
*G01N 15/10*     (2006.01)

(52) U.S. Cl.
CPC .... *G01N 15/1031* (2013.01); *G01N 2015/1087* (2013.01)

(58) Field of Classification Search
CPC .................. G01N 15/1031; G01N 2015/1087; G01N 15/1227
USPC .......... 702/22, 26, 29, 127, 57, 179; 324/71.1
See application file for complete search history.

(56) References Cited

U.S. PATENT DOCUMENTS 3,557,352 A * 1/1971 Hogg et al. ...................... 702/29
3,944,917 A * 3/1976 Hogg et al. ................... 324/71.1

* cited by examiner

*Primary Examiner* — John H Le
(74) *Attorney, Agent, or Firm* — Sughrue Mion, PLLC

(57) ABSTRACT

Provided are a particle measurement apparatus having a plurality of apertures arranged in series therein, and a particle measurement method using the same to statistically analyze multiple signals generated when a particle passes through the plurality of apertures, thus acquiring more accurate information on particles. The particle measurement apparatus includes a plurality of aperture members arranged in series, a plurality of electrodes to form an electric field within the plurality of aperture members, and an analyzer for statistically analyzing multiple electrical signals generated when a particle passes through the plurality of aperture members.

17 Claims, 6 Drawing Sheets

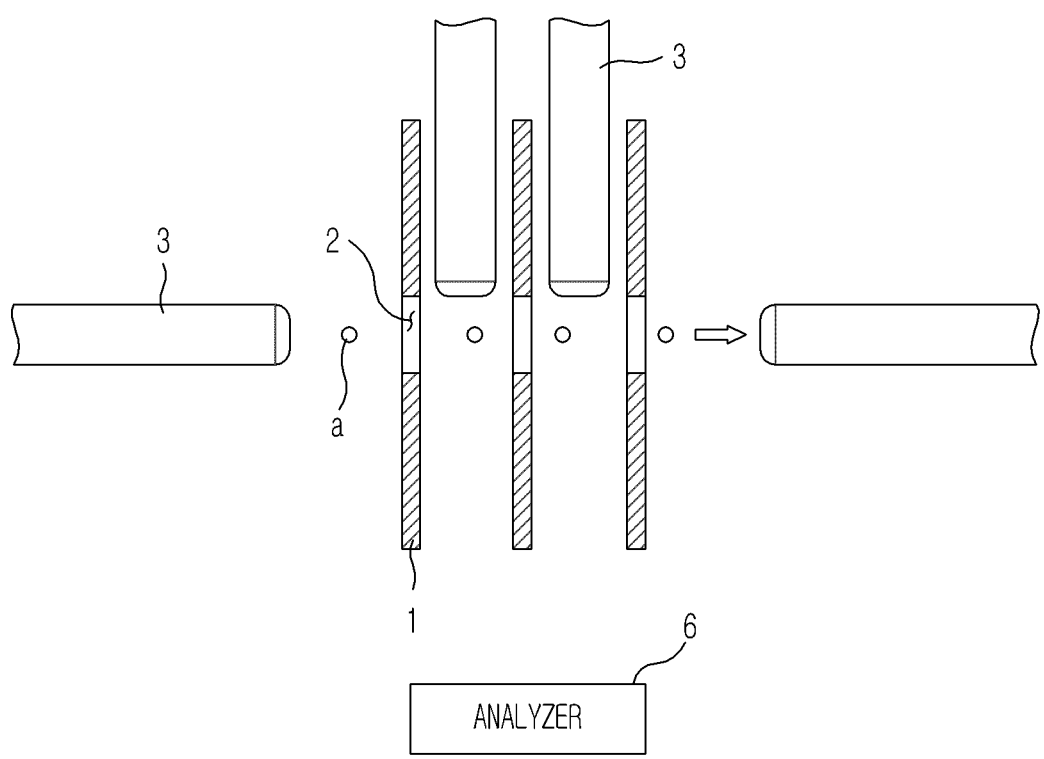

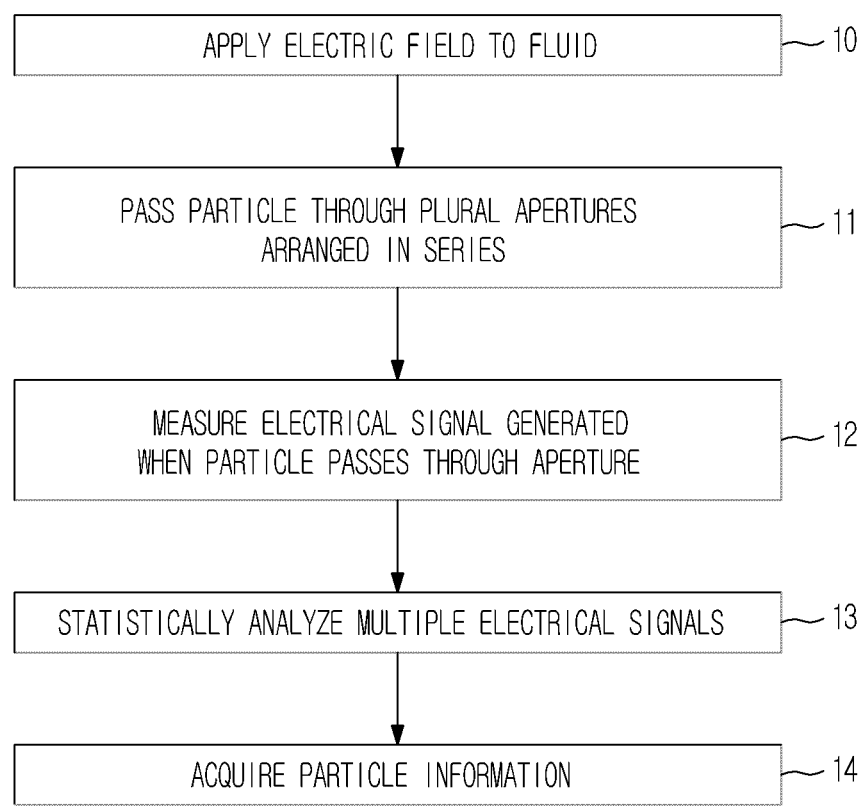

PARTICLE MEASURING APPARATUS AND MEASURING METHOD USING THE SAME

CROSS-REFERENCE TO RELATED APPLICATION

This application claims priority from Korean Patent Application No. 10-2011-0004545 filed Jan. 17, 2011 in the Korean Intellectual Property Office, the disclosure of which is incorporated herein by reference.

BACKGROUND

1. Field

Apparatuses and methods consistent with exemplary embodiments relate to an apparatus for measuring a size and number of particles in a sample and a particle measurement method using the same.

2. Description of the Related Art

An electrical method for measurement of size and/or number of particles in a fluid, in particular, blood cells, is known in the related art. Such an electrical method includes applying an electric field to a fluid containing particles to be measured, and measuring a variation in electrical signals according to voltage, current or resistance altered when the particles pass through a fine hole or aperture. The electrical signals are altered depending upon the size of the particle passing through the aperture. Accordingly, analyzing the foregoing variation may quantify the particles in the fluid with respect to the size thereof.

However, when the particle does not pass through the center of the aperture and/or the shape of the particle is not an perfectly spherical, the detected electrical signals from similar particles may differ.

As a result, even identical particles can cause the problem of decreased accuracy in quantification of particle size.

SUMMARY

Exemplary embodiments provide a particle measurement apparatus having a plurality of apertures arranged in series, and a method for measuring a particle using the foregoing apparatus to statistically analyze multiple signals generated when the particle passes through the plurality of apertures, to thus acquire accurate information about the particle.

According to an aspect of an exemplary embodiment, there is provided a particle measurement apparatus including: a plurality of aperture members arranged in series; a plurality of electrodes configured to form an electric field on the aperture members; and an analyzer configured to statistically analyze multiple electrical signals generated by the electrodes when a particle passes through the plurality of aperture members.

An aperture member may include at least one aperture.

The apertures of each of the plurality of aperture members may have different diameters.

The plurality of aperture members may include apertures having different diameters.

The plurality of aperture members may be spaced apart from one another.

The plurality of electrodes may be located opposite one another while interposing the aperture members therebetween, to form an electric field within the apertures.

The plurality of electrodes may be positioned between each of the plurality of aperture members to form an electric field.

The analyzer may acquire particle information by statistically analyzing the results of multiple electrical signals from the plurality of electrodes.

The particle information may include at least one of the size of a particle and the number of particles.

According to an aspect of another exemplary embodiment, there is provided a particle measurement apparatus including: an aperture member including a plurality of apertures arranged in series; a plurality of electrodes configured to form an electric field on the aperture member; and an analyzer configured to statistically analyze multiple electrical signals generated when a particle passes through the plurality of apertures.

The plurality of apertures may be provided in the form of a tunnel within the aperture member.

The plurality of apertures may be formed spaced apart from one another.

The plurality of apertures may have different diameters.

The plurality of electrodes may be positioned opposite one another while interposing the aperture member therebetween, to form an electric field within the apertures.

The plurality of electrodes may be positioned between each of the plurality of apertures to form an electric field.

The analyzer may acquire particle information by statistically analyzing the results of multiple electrical signals from the plurality of electrodes.

The particle information may include at least one of the size of a particle and the number of particles.

According to an aspect of another exemplary embodiment, there is provided a particle measurement method including: measuring multiple electrical signals generated when a particle passes through a plurality of apertures arranged in series; statistically analyzing the multiple electrical signals; and acquiring particle information based on the analyzed results.

Statistical analysis of the multiple electrical signals includes calculating an average of the multiple electrical signals generated when a particle passes through the plurality of apertures arranged in series.

Acquisition of particle information based on analyzed results includes acquiring particle information which includes at least one of the size of a particle and the number of particles, using statistically analyzed results of the multiple electrical signals.

Thus, use of the plurality of apertures arranged in series to analyze particles may improve the precision and accuracy of measuring particles.

BRIEF DESCRIPTION OF THE DRAWINGS

The above and/or other aspects will become apparent and more readily appreciated from the following description of exemplary embodiments, taken in conjunction with the accompanying drawings of which:

FIGS. 2A and 2B are schematic views illustrating the configuration of a particle measurement apparatus according to another embodiment;

FIG. 4 is a flowchart showing a particle measurement method according to one embodiment of the present invention.

DETAILED DESCRIPTION

Figure 1A:
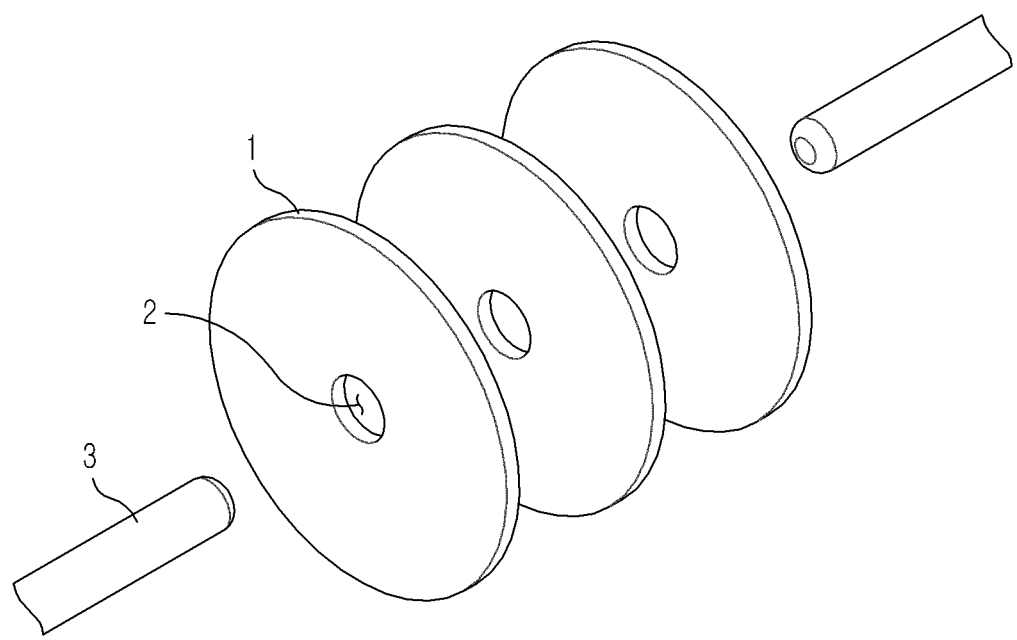
FIGS. 1A and 1B are schematic views illustrating the configuration of a particle measurement apparatus according to one embodiment.

Hereinafter, exemplary embodiments will be described with reference to the accompanying drawings. However, the present invention may be embodied in various other forms, which are not particularly restricted to those described herein.

In the accompanying drawings, like reference numerals denote elements substantially having the same configurations or performing similar functions and actions throughout the drawings.

Figure 1B:
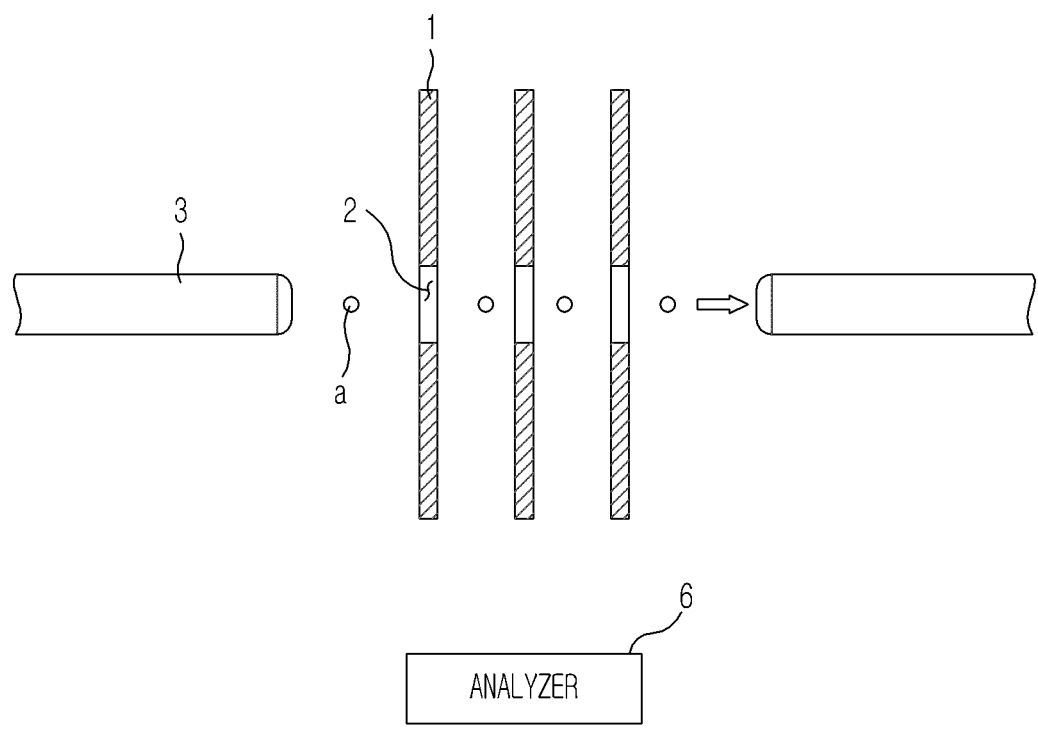

FIGS. 1A and 1B are schematic views illustrating the construction of a particle measurement apparatus according to one embodiment.

The particle measurement apparatus according to an exemplary embodiment may include a plurality of aperture members 1 arranged in series, a pair of electrodes 3 arranged opposite one another with the plurality of aperture members 1 interposed therebetween, and an analyzer 6 which analyzes electrical signals generated when a particle 'a' passes through the plurality of aperture members 1.

An aperture member 1 is a structure having at least one aperture. The plurality of aperture members 1 be arranged in series at predetermined intervals, thereby forming spaces between adjacent aperture members 1.

An aperture 2 is a microfine hole that allows a particle 'a' in a fluid sample to pass therethrough.

The apertures 2 provided in respective aperture members 1 may have different diameters. For example, the aperture in a first aperture member 1 may have a diameter of 90 μm, the aperture in a second aperture member 1 may have a diameter of 80 μm, and the aperture in a third aperture member 1 may have a diameter of 70 μm. However, these are only illustrative examples, without being particularly limited thereto. While each aperture member 1 is shown having a single aperture 2 in the figures, it should be understood that any one or more aperture members 1 may have a plurality of apertures 2, each having different particle diameters.

Referring to the figures, the aperture member 1 is illustrated in disc form, having a predetermined diameter. However, this is only an illustrative example, without being particularly limited thereto. The aperture member 1 may have any configuration wherein a particle 'a' is movable through any of the one or more apertures 2 therein. For instance, the aperture member 1 may have a plurality of barriers formed perpendicular to the flow direction of the fluid being analyzed. The plurality of barriers, which are arranged in series while being spaced apart from one another at predetermined intervals, have one or more apertures 2 therein.

A pair of electrodes 3 may be positioned opposite one another while interposing the plurality of aperture members 1 therebetween. Applying voltage to the pair of electrodes 3 may form an electric field in within the space in which the aperture members 1 are arranged.

The electric field may be formed through the aperture 2. Therefore, when a particle 'a' to be measured passes through the aperture 2, the electric field may undergo changes that may be measured by the particle measurement apparatus, thereby obtaining information about the particle.

Since a plurality of aperture members 1 are arranged in series, if a particle 'a' passes through the plurality of apertures 2 within the aperture members 1 arranged in series, electrical signals may vary corresponding to the number of the aperture members 1 through which the particle passes.

The analyzer 6 detects the multiple electrical signals that occur when the particle 'a' passes through the plurality of aperture members 1, statistically analyzes the detected signals, and produces information about the particle.

For example, if a blood cell passes through three aperture members 1 arranged in series, it may cause a change in the electric field formed within each aperture 2 as it passes therethrough, which in turn, generates three varied electrical signals. The analyzer 6 may then calculate an average of these three signals and determine the size of the particle and the number of particles per particle size.

As discussed above, if a particle 'a' does not pass along a center axis of the aperture 2 (i.e., passes through off-axis) and/or if the particle 'a' does not have perfectly spherical shape, it is difficult to acquire accurate information about the particle using only one electrical signal generated while passing through a single aperture.

Accordingly, if acquisition of information on particle 'a' is executed through statistical analysis of multiple electrical signals, more accurate information about the particle may be acquired, thus enhancing the precision of the measurement apparatus.

Figure 2A:
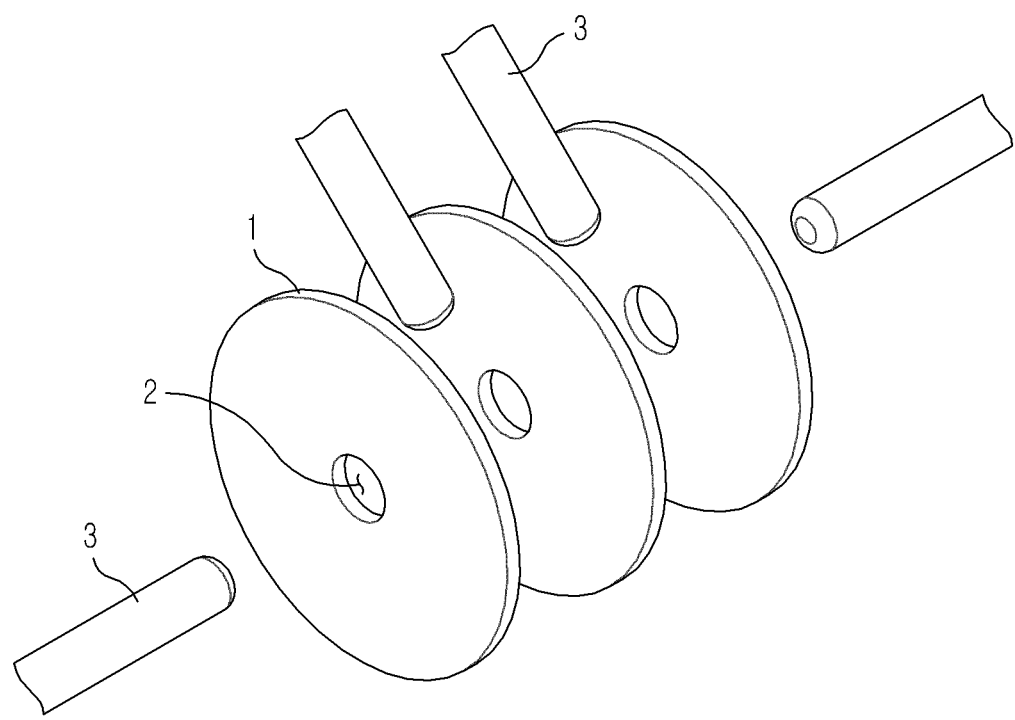

FIGS. 2A and 2B are schematic views illustrating the configuration of a particle measurement apparatus according to another embodiment of the present invention.

According to another exemplary embodiment, there is provided a particle measurement apparatus that includes: a plurality of aperture members 1 arranged in series; a pair of electrodes 3 arranged opposite one another while interposing the plurality of aperture members 1 therebetween, and additional electrodes that are present in the space between each of the plurality of aperture members 1; and an analyzer 6 (not shown) which analyzes electrical signals generated when a particle 'a' passes through each of the plurality of aperture members 1.

Thus, it is possible to generate electrical signals even when a particle 'a' passes through the space between each of the plurality of aperture members 1 using the electric field generated by the electrodes 3 positioned within each of the spaces between each of the aperture members 1. Therefore, when the particle passes through apertures 2 and/or the spaces between each of the plurality of aperture members 1, electrical signals may be generated by the particle measurement apparatus, which are then subject to statistical analysis by the analyzer 6 to acquire information about the particle.

The analyzer 6 may therefore detect multiple electrical signals generated when a particle 'a' passes through the apertures 2 and/or the spaces between each of the aperture members 1, and statistically analyze the detected signals, thereby acquiring information about the particle.

For example, if a blood cell (i.e., particle) passes through three aperture members 1 arranged in series, it may cause a change in the electric field formed within each aperture 2 as the cell passes therethrough, which in turn, generates three varied electrical signals. In addition, when the blood cell passes through the spaces between each of the aperture members 1, it may also cause a change in the electric field formed within the spaces, thereby generating two additional varied electrical signals. The analyzer 6 may then calculate an average of the previous three signals, and optionally include the latter two signals, which were generated as the cell passed through the space between each of the aperture members 1, to determine the size of the particle and the number of particles per particle size.

The other configurations are substantially identical to those illustrated in FIG. 1, therefore, a detailed description thereof will be omitted.

Figure 3:
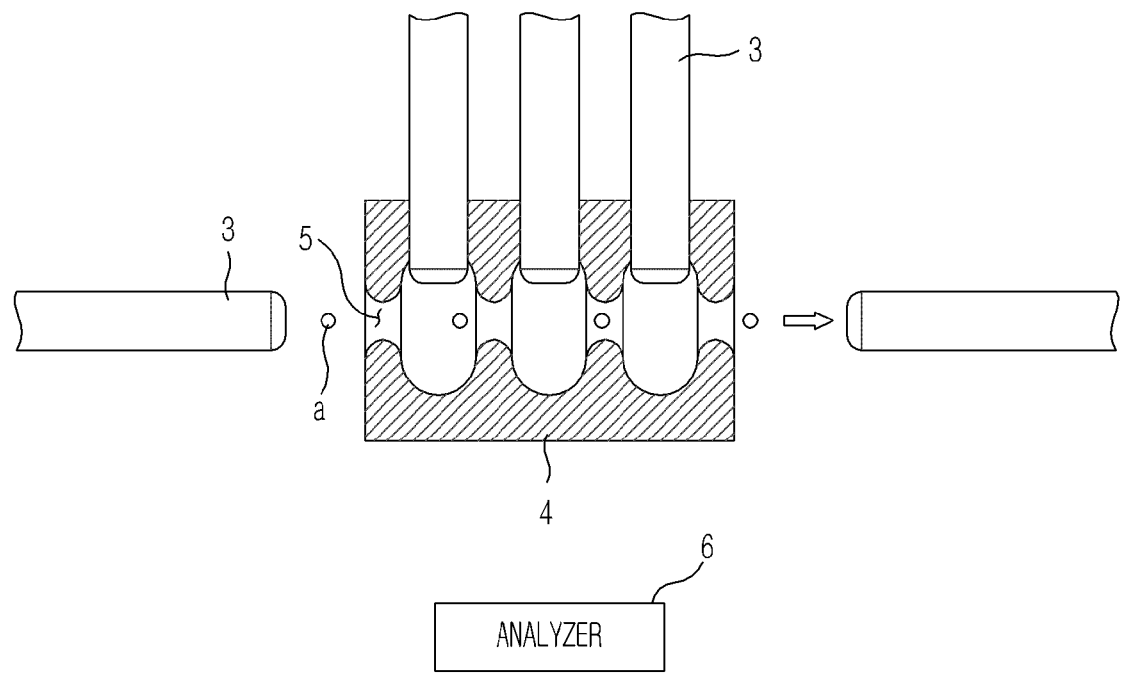
FIG. 3 is a schematic view illustrating the configuration of a particle measurement apparatus according to another embodiment.

FIG. 3 is a schematic view illustrating a particle measurement apparatus according to another embodiment of the present invention.

According to another exemplary embodiment, there is provided a particle measurement apparatus that includes an aperture member 4 including a plurality of apertures 5 arranged in series; a plurality of electrodes 3, which generate an electric field on the aperture member 4; and an analyzer 6 which statistically analyzes the electrical signals generated when a particle 'a' passes through the aperture member 4.

The aperture member 4 is a structure in which apertures 5, such as microfine holes, are arranged in series, that is. In other words, a structure is formed which includes a plurality of apertures 5, which penetrate the inner side of the aperture member 4. Each of the respective apertures 5 are separated from one another by a predetermined interval, wherein the space between each aperture 5 is formed to have a larger diameter than each aperture 5. An electrode 3 may therefore be positioned within each spacing to apply an electric field.

Each of the plurality of apertures 5 in the aperture member 4 may have different diameters from one another.

The electrode 3 may include a pair of electrodes 3 positioned opposite one another while interposing the aperture member 4 therebetween, and may further include a plurality of electrodes 3 positioned within the spaces between each of the plurality of apertures 5 to apply an electric field.

It is therefore possible to generate electrical signals even when a particle 'a' passes through the spaces between each of the plurality of apertures 5 using the electric field generated by the electrodes 3 positioned within the spaces between each of the plurality of apertures 5. Thus, when the particle 'a' passes through apertures 5 and/or the spaces between each of the plurality of apertures 5, electrical signals may be generated by the particle measurement apparatus, which are then subject to statistical analysis by the analyzer 6 to acquire information about the particle.

For example, if a blood cell passes through an aperture member 4 within which four apertures 5 are arranged in series, it may cause a change in the electric field formed within each aperture 5 as the cell passes therethrough, which in turn, generates four varied electrical signals. In addition, when the blood cell passes through the spaces between each of the apertures 5, it may also cause a change in the electric field formed within the spaces, thereby generating three additional varied electrical signals. The analyzer 6 may then calculate an average of the previous four signals and optionally include the latter three signals, which were generated within the spaces between each of the apertures 5, to determine the size of the particle and the number of particles per particle size.

FIG. 4 is a flowchart showing a particle measurement method according to one embodiment of the present invention.

As shown in FIG. 4, an electric field is applied to a fluid including particles 'a' to be analyzed (operation 10).

Voltage is applied to a pair of electrodes 3 arranged while interposing an aperture member 1 or 4 therebetween. In addition, voltage is applied to a plurality of electrodes 3 positioned between each of the plurality of aperture members 1 arranged in series and/or to the plurality of electrodes 3 arranged in the spaces between each of the plurality of apertures 5 formed in series inside the aperture member 4, to thus form an electric field.

When the electric field is applied to the apertures 2 or 5, the fluid containing a particle 'a' passes through the aperture members 1 or 4 (operation 11).

Since the fluid passes through the plurality of aperture members 1 arranged in series or through the aperture member 4 which includes a plurality of apertures 5 arranged in series therein, particles 'a' present in the fluid sequentially pass through the plurality of apertures 2 or 5.

Electric signals generated when a particle 'a' passes through the apertures 2 or 5 are then measured (operation 13).

When the particle 'a' passes through the apertures 2 or 5 in which the electric field is generated, the electric field formed in the apertures 2 or 5 changes, which in turn, generates varied electrical signals corresponding to the changes in the electric fields. In the case where additional electrodes 3 are provided between the aperture members 1 or the apertures 5, additional electrical signals are generated. That is, one particle 'a' passes through a plurality of apertures 2 or 5 arranged in series to generate multiple electrical signals, and the analyzer 6 measures the multiple electrical signals.

The analyzer 6 of the particle measurement apparatus may statistically analyze the multiple electrical signals measured above, thus acquiring information on the particle 'a' (operation 14).

The analyzer 6 measures the multiple electrical signals generated, as a particle 'a' passes through the plurality of apertures 2 or 5 arranged in series, and calculates an average thereof. Based on the average, the size of the particle 'a' may be estimated, which in turn, may be used to determine the number of particles 'a' per particle size.

Although exemplary embodiments have been described above with reference to the accompanying drawings, it is clearly understood that these exemplary embodiments do not particularly restrict the scope of the inventive concept. Accordingly, it would be appreciated by those skilled in the art that various substitutions, variations and/or modifications may be made in these exemplary embodiments without departing from the principles and spirit of the inventive concept. Therefore, it is obviously understood that the inventive concept is not restricted to technical configurations and arrangements illustrated above.

What is claimed is:

1. A particle measurement apparatus comprising:
a plurality of aperture members arranged in series;
a plurality of electrodes configured to form an electric field in the plurality of aperture members; and
an analyzer configured to statistically analyze multiple electrical signals representative of particles in a fluid generated when the fluid passes through the plurality of aperture members while the electric field is formed,
wherein the plurality of aperture members are arranged apart from one another, and each aperture member includes at least one aperture.

2. The particle measurement apparatus according to claim 1, wherein the apertures of the plurality of aperture members have different diameters.

3. The particle measurement apparatus according to claim 1, wherein the plurality of aperture members includes apertures having different diameters.

4. The particle measurement apparatus according to claim 1, wherein the aperture members are interposed between the plurality of electrodes, and the plurality of electrodes are configured to form an electric field within each aperture.

5. The particle measurement apparatus according to claim 1, wherein the plurality of electrodes are positioned between each of the plurality of aperture members to form an electric field.

6. The particle measurement apparatus according to claim 1, wherein the analyzer is configured to acquire information about the particle passing through the plurality of aperture members based on results of statistical analysis of the multiple electrical signals.

7. The particle measurement apparatus according to claim 6, wherein the particle information includes at least one of a size and a number of the particles.

8. A particle measurement apparatus comprising:
an aperture member including a plurality of apertures arranged in series;

a plurality of electrodes configured to form an electric field within the aperture member; and an analyzer configured to statistically analyze multiple electrical signals representative of particles in a fluid generated when the fluid passes through the plurality of apertures while the electric field is formed, wherein the analyzer is configured to acquire information about the particles passing through the aperture member using results of statistical analysis of the multiple electrical signals, and the particle information includes a number of the particles.

9. The particle measurement apparatus according to claim 8, wherein the plurality of apertures are formed in a tunnel shape inside the aperture member.

10. The particle measurement apparatus according to claim 8, wherein the plurality of apertures are formed apart from one another.

11. The particle measurement apparatus according to claim 8, wherein each of the apertures have different diameters.

12. The particle measurement apparatus according to claim 8, wherein the aperture member is interposed between the plurality of electrodes, and the plurality of electrodes are configured to form an electric field within each of the apertures.

13. The particle measurement apparatus according to claim 8, wherein the plurality of electrodes are positioned between each of the plurality of apertures to form an electric field.

14. The particle measurement apparatus according to claim 8, wherein the particle information includes a size of the particles.

15. A particle measurement method by a processor comprising:

applying a voltage to a plurality of electrodes to form an electric field in a plurality of apertures arranged in series and spaced apart from one another;

measuring multiple electrical signals representative of particles in a fluid generated when the fluid passes through the plurality of apertures while the electric field is formed;

statistically analyzing the multiple electrical signals; and acquiring particle information based on results of the analyzing.

16. The method according to claim 15, wherein statistical analyzing the multiple electrical signals comprises determining an average of the multiple electrical signals generated when a particle passes through the plurality of apertures arranged in series.

17. The method according to claim 15, wherein the particle information includes size of the particles and a number of the particles.

* * * * *